US006562317B2

(12) United States Patent
Greff et al.

(10) Patent No.: US 6,562,317 B2
(45) Date of Patent: May 13, 2003

(54) RADIOACTIVE EMBOLIZING COMPOSITIONS

(75) Inventors: Richard J. Greff, St. Pete Beach, FL (US); George Wallace, Coto de Caza, CA (US)

(73) Assignee: Micro Therapeutics, Inc., San Clemente, CA (US)

( * ) Notice: Subject to any disclaimer, the term of this patent is extended or adjusted under 35 U.S.C. 154(b) by 0 days.

(21) Appl. No.: 09/785,274

(22) Filed: Feb. 20, 2001

(65) Prior Publication Data

US 2001/0009656 A1 Jul. 26, 2001

Related U.S. Application Data

(62) Division of application No. 09/393,886, filed on Sep. 10, 1999, now Pat. No. 6,218,315, which is a continuation of application No. 08/962,819, filed on Nov. 3, 1997, now Pat. No. 6,015,541.

(51) Int. Cl.[7] .......................... A61K 51/00; A61N 5/00
(52) U.S. Cl. ...................... 424/1.25; 424/1.11; 600/3; 600/4
(58) Field of Search ..................... 424/1.25, 1.33, 424/1.29, 9.4, 1.11; 600/3, 4

(56) References Cited

U.S. PATENT DOCUMENTS

| | | | |
|---|---|---|---|
| 3,527,224 A | | 9/1970 | Rabinowitz et al. |
| 3,591,676 A | | 7/1971 | Hawkins et al. |
| 4,268,495 A | | 5/1981 | Muxfeldt et al. |
| 4,795,741 A | | 1/1989 | Leschiner et al. |
| 4,938,763 A | | 7/1990 | Dunn et al. |
| 5,383,899 A | * | 1/1995 | Hammerslag ............... 606/214 |
| 5,443,454 A | | 8/1995 | Tanabe et al. |
| 5,514,379 A | | 5/1996 | Weissleder et al. |
| 5,582,568 A | | 12/1996 | Greff et al. |
| 5,667,767 A | | 9/1997 | Greff et al. |
| 5,695,480 A | | 12/1997 | Evans et al. |
| 5,762,903 A | | 6/1998 | Park et al. |
| 5,942,209 A | * | 8/1999 | Leavitt et al. .............. 424/1.25 |

FOREIGN PATENT DOCUMENTS

| | | |
|---|---|---|
| EP | 0 927 558 | 7/1999 |
| WO | WO 97/07783 | 3/1997 |
| WO | WO 97/45131 | 4/1997 |
| WO | WO 98/04312 | 2/1998 |
| WO | WO 99/43366 | 9/1999 |

OTHER PUBLICATIONS

"Cancer, Principles & Practice of Oncology", 4th Ed., vol. 1, "Cancer Treatment", pp. 545–548 (1993).
Casarett and Doull's Toxicology, Amdur, et al., Editors, Pergamon Press, New York, pp. 661–664 (1975).
Castaneda–Zuniga, et al., "Interventional Radiology", in Vascular Publishers (1992).
Encyclopedia of Medical Devices and Instrumentation, J.G. Webster, Editor (1988) 4:2456.
Hellman, "Cancer, Principles & Practice of Oncology", 4th Ed., vol. 1, Chapter 15, Principles of Radiation Therapy, pp. 248–250 (1993).
Kinugasa, et al., "Early Treatment of Subarachnoid Hemorrhage After Preventing Rerupture of an Aneurysm", J. Neurosurg., 83:34–41 (1995).
Kinugasa, et al., "Prophylactic Thrombosis to Prevent New Bleeding and to Delay Aneurysm Surgery", Neurosurg., 36:661 (1995).
Kinugasa, et al., "Direct Thrombois of Aneurysms with Cellulose Acetate Polymer", J. Neurosurg., 77:501–507 (1992).
Mandai, et al., "Direct Thrombosis of Aneurysms with Cellulose Acetate Polymer", J. Neurosurg., 77:497–500 (1992).
Sitton, "Early and Late Radiation–Induced Skin Alterations Part I:Mechanisms of Skin Changes", Oncology Nursing Forum, 19(5):801–807 (1992).
Taki, et al., "Selection and Combination of Various Endovascular Techniques in the Treatment of Giant Aneurysms", J. Neurosurg., 77:37–42 (1992).
Copy of European Search Report dated Oct. 16, 2002.

* cited by examiner

Primary Examiner—Michael G. Hartley
(74) Attorney, Agent, or Firm—Burns, Doane, Swecker & Mathis L.L.P.

(57) ABSTRACT

Disclosed are novel radioactive compositions which are particularly suited for treating solid mass tumors via catheter delivery.

20 Claims, No Drawings

RADIOACTIVE EMBOLIZING COMPOSITIONS

This application is a divisional of application Ser. No. 09/393,886, filed Sep. 10, 1999, U.S. Pat. No. 6,214,315, which is a continutation of application Ser. No. 08/962,819. filed Nov. 3, 1997. issued as U.S. Pat. No. 6,015,541.

BACKGROUND OF THE INVENTION

1. Field of the Invention

This invention is directed to novel compositions for delivery in vivo and preferably to vascular sites. Such compositions are particularly suited for treating solid mass tumors via catheter delivery of the composition to a vascular site leading to or in the solid mass tumor and subsequent embolization of this vascular site.

In particular, the compositions of this invention comprise a biocompatible polymer, a biocompatible solvent and a radioactive agent which provides therapeutic doses of radiation.

REFERENCES

The following publications are cited in this application as superscript numbers:

[1] Mandai, et al., "Direct Thrombosis of Aneurysms with Cellulose Acetate Polymer", *J. Neurosurg.*, 77:497–500 (1992)

[2] Kinugasa, et al., "Direct Thrombois of Aneurysms with Cellulose Acetate Polymer", *J. Neurosurg.*, 77:501–507 (1992)

[3] Casarett and Doull's *Toxicology*, Amdur, et al., Editors, Pergamon Press, New York, pp. 661–664 (1975)

[4] Greff, et al., U.S. Pat. No. 5,667,767, for "Novel Compositions for Use in Embolizing Blood Vessels", issued Sep. 16, 1997

[5] Greff, et al., U.S. Pat. No. 5,580,568 for "Cellulose Diacetate Compositions for Use in Embolizing Blood Vessels", issued Dec. 3, 1996

[6] Kinugasa, et al., "Early Treatment of Subarachnoid Hemorrhage After Preventing Rerupture of an Aneurysm", *J. Neurosurg.*, 83:34-41 (1995)

[7] Kinugasa, et al., "Prophylactic Thrombosis to Prevent New Bleeding and to Delay Aneurysm Surgery", *Neurosurg.*, 36:661 (1995)

[8] Taki, et al., "Selection and Combination of Various Endovascular Techniques in the Treatment of Giant Aneurysms", *J. Neurosurg.*, 77:37–24 (1992)

[9] Evans, et al., U.S. patent application Ser. No. 08/802,252 for "Novel Compositions for Use in Embolizing Blood Vessels", filed Feb. 19, 1997

[10] Castaneda-Zuniga, et al., *Interventional Radiology*, in Vascular Embolotherapy, Part 1, 1:9–32, Williams & Wilkins, Publishers (1992)

[11] Rabinowitz, et al., U.S. Pat. No. 3,527,224 for "Method of Surgically Bonding Tissue Together", issued Sep. 8, 1970

[12] Hawkins, et al., U.S. Pat. No. 3,591,676 for "Surgical Adhesive Compositions", issued Jul. 6, 1971

[13] Encyclopedia of Medical Devices and Instrumentation, J. G. Webster, Editor (1988) 4:2456

[14] Tanabe, U.S. Pat. No. 5,443,454 for "Catheter for Embolectomy", issued Aug. 22, 1995

[15] Sitton, *"Early and Late Radiation-Induced Skin Alterations Part I:Mechanisms of Skin Changes"*, Oncology Nursing Forum, 19(5): 801–807 (1992)

[16] Dunn, et al., U.S. Pat. No. 4,938,763 for "Biodegradable In-Situ Forming Implants and Methods of Producing Same", issued Jul. 3, 1990

[17] Hellman, *"CANCER, Principles & Practice of Oncology"*, 4th Ed., Volume 1, Chapter 15, *"Principles of Radiation Therapy"*, pp. 248–250 (1993)

[18] *"CANCER, Principles & Practice of Oncology"*, 4th Ed., Volume 1, *"Cancer Treatment"*, pp. 545–548 (1993)

All of the above publications are herein incorporated by reference in their entirety to the same extent as if each individual reference was specifically and individually indicated to be incorporated herein by reference in its entirety.

2. State of the Art

Current therapeutic regimens for treating solid mass tumors in mammals include radiation therapy, vascular embolization, chemotherapy with cytotoxic agents, open surgery, and the like as well as combinations of two or more of the above.

Radiation therapy includes both the external and internal exposure of the tumor to ionizing radiation to induce tumor necrosis. In a first instance, application of external sources of radiation, known as teletherapy, has been used to treat solid mass tumors. Such external radiation sources include X-rays from a linear accelerator, gamma-rays generated from isotopes such as cobalt-60 (administered with a telecobalt apparatus) and electron beams generated from specialized radiotherapy machines or high energy linear accelerators. The use of external sources of radiation requires careful preplanning so that the patient is placed in the exact position necessary to treat the solid mass tumor. The precise positioning of the patient and application of radiation is important so as to minimize irradiation and tissue damage to unintended areas of the body. Nevertheless, external irradiation of the tumor induces skin damage to the exposed skin[15] and is not amenable to deep tumors because the external radiation gives unwanted tissue absorption around the tumor area.

Another technique, brachytherapy, is internal radiotherapy on solid mass tumors in a mammal by the in vivo placement of radioactive sources close to or in the tumor where destruction of non-cancerous tissue is limited.[17] Specifically, the dose distribution of the radiation is determined by the inverse square law and, accordingly, radiation effects on tissues at any distance from the radioactive source is limited. Examples of brachytherapy are interstitial or intracavitary radiation used in the treatment of many urologic, lung, gynecological and oral tumors. In one example of this technique, a removable applicator is used to direct radiation to desired areas while limiting exposure to other tissues. Nevertheless, brachytherapy is not amenable to tumors inaccessible by conventional surgical techniques.

Still another technique for the treatment of solid mass tumors is vascular embolization of blood vessels feeding the tumor to induce necrosis of the tumor tissue by obstructing its arterial supply. One preferred example of this technique is direct embolization of blood vessels by, e.g., catheter techniques which permit the selective placement of the catheter at the vascular site to be embolized which can be as small as 1 mm in diameter.

Preferred embolic compositions for catheter delivery to the vascular site include a biocompatible solvent, a biocompatible polymer and a contrast agent.[1–8, 14] The biocompatible solvent is miscible or soluble in blood or other body fluid and also solubilizes the biocompatible polymer during delivery. The biocompatible polymer is selected to be soluble in the biocompatible solvent but insoluble in blood or other body fluid. The contrast agent is selected to permit the physician to fluoroscopically visualize delivery of this composition. Upon contact with the blood or other body fluids, the biocompatible solvent dissipates from the embolic composition whereupon the biocompatible polymer precipitates in the presence of the water insoluble contrast agent and embolizes the blood vessel.

The use of vascular embolization, by itself, in the treatment of solid mass tumors is complicated by the fact that, upon embolization of the blood vessel feeding the tumor, alternative vascular routes can be generated by the tumor which continue to feed the tumor.

Another example of embolization techniques in the treatment of solid mass tumors is termed "chemoembolization" which combines the use of intra-arterial high-dose chemotherapy with obstruction of the tumor vascular bed to provide a two-prong attack on the tumor.[17] The chemotherapeutic agent leaches from the deposited embolic agent to provide prolonged exposure time of the tumor to the chemotherapeutic agent and the embolic agent adds an ischemic component to enhance tumor necrosis. One example of this technique includes the placement of particulate carriers with chemotherapeutic agents bound to microspheres or contained in microcapsules (e.g., liposomes) at the vascular site.

However, the chemotherapeutic agent is susceptible to migration and systemic delivery in vivo with potential side effects in the patient.

In view of the above, there exists a continuing need to improve the treatment regimens for therapeutically treating solid mass tumors and, in particular, in vivo treatment of such tumors.

SUMMARY OF THE INVENTION

This invention is directed to novel embolic compositions comprising a radioactive agent which are delivered e.g., to the vascular site, as a fluid and which solidify in vivo to form a solid, coherent mass. In a preferred embodiment, these compositions are employed in novel methods to embolize blood vessels supplying blood to a solid mass tumor as well as to provide therapeutic levels of radiation to the blood vessel and/or surrounding tissue. These novel methods allow for treatment of otherwise inoperable tumors by the catheter delivery of such embolic compositions to vascular sites.

Accordingly, in one of its composition aspects, this invention is directed to a composition comprising:
(a) a biocompatible polymer;
(b) a biocompatible solvent; and
(c) from about 0.1 to about 25 weight percent of a water insoluble radioisotope having a radioactive content of from about 0.5 microcurie to about 100 millicuries.

In a preferred embodiment, the amount and radioactive content of the radioisotope is sufficient to provide for a cumulative ionizing radiation dosage at the site of implantation in a mammalian subject of from about 200 to about 10,000 rads [2–100 Gray (Gy)].

In a more preferred embodiment, these compositions are employed to effect necrosis of at least a portion of a solid mass tumor in the mammal. Accordingly, these compositions are delivered, for example, directly to the solid mass tumor or to a vascular site selected to be in or near the solid mass tumor and the amount and radioactive content of the radioisotope employed in the composition is sufficient to effect such necrosis.

Accordingly, in one of its method aspects, this invention is directed to a method for embolizing a blood vessel leading to or in a solid mass tumor in a mammal and causing necrosis to a portion of said solid mass tumor which method comprises:
(a) identifying a blood vessel in said mammal which leads to or is in the solid mass tumor;
(b) injecting a sufficient amount of an embolic composition comprising a biocompatible polymer, a biocompatible solvent and a water insoluble radioisotope into said blood vessel under conditions wherein a precipitate is formed which embolizes the blood vessel and further wherein the radioisotope is employed in an amount effective to cause necrosis of at least a portion of said tumor.

In another of its method aspects, this invention is directed to a method for causing necrosis to a portion of a solid mass tumor which method comprises:
(a) identifying a solid mass tumor in a mammal;
(b) injecting a sufficient amount of an embolic composition comprising a biocompatible polymer, a biocompatible solvent and a water insoluble radioisotope into said tumor under conditions wherein a precipitate is formed wherein the radioisotope is employed in an amount effective to cause necrosis of at least a portion of said tumor.

The biocompatible polymer employed in these compositions and methods can be either a biodegradable polymer or a non-biodegradable polymer but is, preferably, a non-biodegradable polymer.

In one embodiment, the radioisotope acts as a contrast agent to permit visualization of the composition during catheter delivery. Alternatively, a non-radioactive contrast agent is employed in combination with the radioisotope in order to ensure visualization.

In another embodiment, the biocompatible polymer can be replaced with a biocompatible prepolymer and, when so used, the presence of the biocompatible solvent becomes optional. In this embodiment, this invention is directed to a composition comprising:
(a) a biocompatible prepolymer;
(b) an optional biocompatible solvent; and
(c) from about 0.1 to about 25 weight percent of a water insoluble radioisotope having a radioactive content of from about 0.5 microcurie to about 100 millicurie.

In addition, this invention is also directed to a method for embolizing a blood vessel leading to or in a solid mass tumor in a mammal and causing necrosis to a portion of said solid mass tumor which method comprises:
(a) identifying a blood vessel in said mammal which leads to or is in the solid mass tumor;
(b) injecting a sufficient amount of an embolic composition comprising a biocompatible prepolymer, a water insoluble radioisotope and optionally a biocompatible solvent into said blood vessel under conditions wherein the prepolymer polymerizes to form a solid mass which embolizes the blood vessel and further wherein the radioisotope is employed in an amount effective to cause necrosis of at least a portion of the tumor,
wherein said delivery is conducted under conditions wherein said prepolymer polymerizes in situ, in the presence of the water insoluble contrast agent, at the vascular site thereby embolizing the blood vessel.

In a preferred embodiment, the biocompatible solvent is dimethylsulfoxide (DMSO), ethanol or acetone.

In one embodiment, the radioisotope acts as a contrast agent to permit visualization of the composition during catheter delivery. Alternatively, a non-radioactive contrast agent is employed in combination with the radioisotope in order to ensure visualization.

DETAILED DESCRIPTION OF THE INVENTION

This invention is directed to novel compositions which are particularly suitable for treating solid mass tumors via delivery of the composition either directly to the solid mass tumor or to a vascular site leading to or in the solid mass tumor and subsequent embolization of this vascular site while, in either case, delivering a therapeutically effective amount of radiation to the solid mass tumor.

However, prior to discussing this invention in further detail, the following terms will first be defined:

The term "embolizing" as used in conjunction with "embolizing compositions" and "embolizing agents" refers to a process wherein a material is injected into a blood vessel which thereafter fills or plugs the blood vessel so that blood flow through the vessel ceases.

Embolization is used to ablate diseased tissue (e.g., tumors, etc.) by cutting off its blood supply. Traditionally, in the case of, for example, tumors, catheter embolization is used to induce necrosis of the tumor by obstructing its arterial supply. Needles may also be used to inject the embolic compositions of this invention into the appropriate vascular sites as well as directly into the solid tumor mass. Embolization may entail deliberate sacrifice of the organ harboring the tumor, as in embolization of renal cancers. However, in the liver with its dual blood supply, a tumor can be embolized through the hepatic artery while the normal hepatic parenchyma is sustained by portal venous inflow.

The term "solid mass tumor" refers to cancerous and non-cancerous conditions manifested by a solid mass growth as opposed to conditions lacking such a solid mass growth, e.g., leukemia. Various types of solid mass tumors may be treated with the compositions and methods of this invention including both cancerous and benign tumors. Examples of cancerous solid mass tumors include, for instance, lung cancer, cervical cancer, soft tissue sarcomas, and kidney and liver tumors. Examples of benign tumors include benign brain tumors, uterine fibroid tumors, and the like.

The term "biocompatible polymer" refers to polymers which, in the amounts employed, are non-toxic and substantially non-immunogenic when used internally in the patient and which are substantially insoluble in blood. The biocompatible polymer can be either biodegradable or, preferably, non-biodegradable.

Biodegradable polymers are disclosed in the art.[16,18] For example, Dunn, et al.[16] discloses the following examples of biodegradable polymers: linear-chain polymers such as polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), polyvinylpyrrolidone, polyethylene glycol, polyhydroxycellulose, chitin, chitosan, and copolymers, terpolymers and combinations thereof. Other biodegradable polymers include, for example, gelatin, collagen, etc.[18]

Suitable non-biodegradable biocompatible polymers include, by way of example, cellulose acetates[2,6-7] (including cellulose diacetate[5]), ethylene vinyl alcohol copolymers[4,8], hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof[9].

Preferably, the biocompatible polymer employed does not cause an adverse inflammatory reaction when employed in vivo. The particular biocompatible polymer employed is selected relative to the viscosity of the resulting polymer solution, the solubility of the biocompatible polymer in the biocompatible solvent, and the like. For example, the selected biocompatible polymer should be soluble in the amounts employed in the selected biocompatible solvent and the resulting composition should have a viscosity suitable for in vivo delivery either by catheter or by injection. Such factors are well within the skill of the art.

Preferred biocompatible polymers include cellulose diacetate and ethylene vinyl alcohol copolymer. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to about 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by merely adjusting the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the embolizing properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 5 weight percent of the ethylene vinyl alcohol copolymer, 20 weight percent of a tantalum contrast agent in DMSO has a viscosity equal to or less than 60 centipoise at 20° C. As is apparent to one skilled in the art, with all other facts being equal, copolymers having a lower molecular weight will impart a lower viscosity to the composition as compared to higher molecular weight copolymers. Accordingly, adjustment of the viscosity of the composition as necessary for catheter delivery can be readily achieved by merely adjusting the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous environment (e.g., blood or tissue). In a particularly preferred embodiment, the copolymers employed herein comprise a mole percent of ethylene of from about 25 to about 60 and a mole percent of vinyl alcohol of from about 40 to about 75. These compositions provide for requisite precipitation rates suitable for use in embolizing blood vessels.

The term "contrast agent" refers to a biocompatible radiopaque material capable of being monitored during injection into a mammalian subject by, for example, radiography. The contrast agent can be either water soluble or water insoluble and preferably does not contain radioactivity above the native or endogenous amounts naturally occurring in the elements employed (i.e., are "non-radioactive").

Examples of water soluble contrast agents include metrizamide, iopamidol, iothalamate sodium, iodomide sodium, and meglumine. Examples of water insoluble contrast agents include tantalum, tantalum oxide, and barium sulfate, each of which is commercially available in the proper form for in vivo use including a preferred particle size of about 10 $\mu$m or less. Other water insoluble contrast agents include gold, tungsten, and platinum powders.

Preferably, the contrast agent is water insoluble (i.e., has a water solubility of less than 0.01 mg/ml at 20° C.).

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, acetone, and the like. Aqueous mixtures with the biocompatible solvent can also be employed provided that the amount of water employed is sufficiently small that the dissolved polymer precipitates upon contact with the blood. Preferably, the biocompatible solvent is dimethylsulfoxide.

The term "encapsulation" as used relative to the contrast agent being encapsulated in the polymer precipitate is not meant to infer any physical entrapment of the contrast agent within the precipitate much as a capsule encapsulates a medicament. Rather, this term is used to mean that an integral coherent precipitate forms which does not separate into individual components.

The term "biocompatible prepolymer" refers to materials which polymerize in situ to form a polymer and which, in the amounts employed, are non-toxic and substantially non-immunogenic when used internally in the patient and which are substantially insoluble in blood. Suitable biocompatible prepolymers include, by way of example, cyanoacrylates[10, 11, 12], (C1–C6)hydroxyalkyl (C1–C6)alkacrylate (e.g., hydroxyethyl methacrylate), silicon prepolymers, and the like. The prepolymer can either be a monomer or a reactive oligomer[12]. Preferably, the biocompatible prepolymer does not cause an adverse inflammatory reaction when employed in vivo.

The term "radioisotope" refers to naturally or non-naturally occurring water insoluble radioisotopes conventionally employed in nuclear medicine including, by way of example only, $^{90}$yttrium, $^{192}$iridium, $^{198}$gold, $^{125}$iodine, $^{137}$cesium, $^{60}$cobalt, $^{55}$cobalt, $^{56}$cobalt, $^{57}$cobalt, $^{52}$magnesium, $^{55}$iron, $^{32}$phosphorus, and $^{90}$strontium. Other radionuclides currently being produced for use in nuclear medicine include, for example, $^{81}$rubidium, $^{206}$bismuth, $^{67}$gallium, $^{77}$bromine, $^{129}$cesium, $^{73}$selenium, $^{72}$selenium, $^{72}$arsenic, $^{103}$palladium, $^{203}$lead, $^{111}$indium, $^{52}$iron, $^{167}$thulium, $^{57}$nickel, 62zinc, $^{61}$copper, $^{201}$thallium, and $^{123}$iodine. Each of these isotopes can be made by standard techniques well known in the art[13]. Additionally, radioisotopes which are water soluble or water reactable are typically used as water insoluble salts.

In one embodiment, radioisotopes having a sufficiently high atomic number so as to be radiopaque can be used to serve both as a source of radiation and as a water insoluble contrast agent for detection under fluoroscopy.

In another embodiment, a separate non-radioactive contrast agent is employed in conjunction with the radioisotope.

The term "absorbed dose" or "radiation dose" refers to the dose of radiation typically employed by the attending oncologist in treating solid mass tumors. The radiation dose is defined in terms of energy deposited per unit mass, given in the following units: 1 Gray (Gy)=1 Joule per kilogram. In the past, the standard unit of radiotherapy was 1 rad, and 1 Gy=100 rads.

Compositions

The polymer or prepolymer compositions employed in the methods of this invention are prepared by conventional methods whereby each of the components is added and the resulting composition mixed together until the overall composition is substantially homogeneous.

For example, polymer compositions can be prepared by adding sufficient amounts of the biocompatible polymer to the biocompatible solvent to achieve the effective concentration for the polymer composition. Preferably, the polymer composition will comprise from about 2.5 to about 8.0 weight percent of the biocompatible polymer composition based on the total weight of the polymer composition and more preferably from about 4 to about 5.2 weight percent. If necessary, gentle heating and stirring can be used to effect dissolution of the biocompatible polymer into the biocompatible solvent, e.g., 12 hours at 50° C.

Where a separate non-radioactive contrast agent is employed, sufficient amounts of this contrast agent are then added to the biocompatible solvent to achieve the effective concentration for the complete composition. Preferably, the composition will comprise from about 7 to about 40 weight percent of total contrast agent (non-radioactive contrast agent plus any radiopaque radioisotope) and more preferably from 5 about 14 to about 30 weight percent and even more preferably about 22 weight percent.

When a water soluble non-radioactive contrast agent is employed, the agent is typically soluble in the solution comprising the non-aqueous solvent and stirring is effected to render the composition homogeneous.

When a water insoluble non-radioactive contrast agent is employed, the agent is insoluble in the biocompatible solvent, and stirring is employed to effect homogeneity of the resulting suspension. In order to enhance formation of the suspension, the particle size of the water insoluble non-radioactive contrast agent is preferably maintained at about 10 $\mu$m or less and more preferably at from about 1 to about 5 $\mu$m (e.g., an average size of about 2 $\mu$m).

In one embodiment, a non-radioactive contrast agent having a particle size of less than 10 $\mu$m is prepared, for example, by fractionation. In such an embodiment, a non-radioactive water insoluble contrast agent such as tantalum, having an average particle size of less than about 20 $\mu$m, is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition can be heat sterilized and then stored preferably in sealed bottles or vials (e.g., amber bottles) until needed.

Each of the polymers recited herein is commercially available or can be prepared by methods well known in the art. For example, polymers are typically prepared by conventional techniques such as radical, thermal, UV, $\gamma$ irradiation, or electron beam induced polymerization employing, as necessary, a polymerization catalyst or polymerization initiator to provide for the polymer composition. The specific manner of polymerization is not critical and the polymerization techniques employed do not form a part of this invention.

In order to maintain solubility in the biocompatible solvent, the polymers described herein are preferably not cross-linked.

Prepolymer compositions can be prepared by adding sufficient amounts of any non-radioactive contrast agent employed in the liquid (e.g., liquid prepolymer) to achieve the effective concentration for the complete polymer composition. Preferably, the total contrast agent (non-radioactive contrast agent plus any radiopaque radioisotope) will comprise from about 7 to about 40 weight percent of the prepolymer composition based on the total weight of the composition and more preferably from about 14 to about 30 weight percent and even more preferably about 22 weight percent.

When a non-radioactive contrast agent is used which is not soluble in the biocompatible prepolymer composition, stirring is employed to effect homogeneity of the resulting suspension. In order to enhance formation of the suspension, the particle size of the insoluble non-radioactive contrast agent is preferably maintained at about 10 $\mu$m or less and more preferably at from about 1 to about $\mu$m (e.g., an average size of about 2 $\mu$m).

When the prepolymer is liquid (as in the case of cyanoacrylates or silicone), the use of a biocompatible solvent is not strictly necessary but may be preferred to provide for an appropriate viscosity, for an appropriate curing time, etc. in the embolic composition. Preferably, when employed, the biocompatible solvent will comprise from about 30 to about 90 weight percent of the biocompatible prepolymer composition based on the total weight of the prepolymer composition and more preferably from about 60 to about 80 weight percent. When a biocompatible solvent is employed, the prepolymeric composition typically comprises from about 10 to about 50 weight percent of the prepolymer based on the total weight of the composition.

Suitable solvents include iodinated soy bean or poppy seed oil for cyanoacrylates and water for hydroxyacrylics such as hydroxyethyl methacrylate. In such cases, the oil acts both as a carrier for the prepolymer, a contrast agent and a polymerization time modifier. Other solvents include hexamethyldisiloxane which is preferably employed in conjunction with silicone.

In a particularly preferred embodiment, the prepolymer is cyanoacrylate which is preferably employed in the absence of a biocompatible solvent. When so employed, the cyanoacrylate adhesive is selected to have a viscosity of from about 5 to about 20 centipoise at 20° C.

The radioisotope is preferably added to the otherwise complete composition immediately prior to the administration of the composition to the patient in order to reduce exposure of radiation to the clinician. In a preferred embodiment, the radioisotope is $^{192}$iridium, $^{198}$gold, $^{125}$iodine, $^{137}$cesium or $^{60}$cobalt. The radioisotope is preferably selected relative to the type and size of the solid mass tumor and its location in the patient. This material may also be used as part of or the entire contrast agent to aid in the placement of the composition to cause necrosis to at least a portion of the tumor.

Treatment dosages of radiation employed in a particular patient are, of course, dependent upon the judgment of the attending clinician and nuclear medicine professional depending upon factors such as the type and severity of the solid mass tumor in the patient, the age, weight and general condition of the patient, the toxicity and/or side effects due to the radiation treatment and the like. Such factors are well known to the skilled artisan. In some cases, it may be necessary or desirable only to embolize and necrosis blood vessel(s) leading to or located in the solid mass tumors and, accordingly, appropriate radiation levels are selected relative to such a result.

Preferably, however, the composition is employed to both embolize the blood vessel and to cause necrosis of at least a portion of the tumor. When so employed, appropriate radiation levels are selected to effect such a result. While there is no consensus on the ideal radiotherapy prescription for a particular tumor type, a number of prescriptions are currently used based either on the principle of administering a high dose which requires multiple fractions over a relatively long time or short treatment time in relatively large fractions. For example, 64 Gy in 32 fractions over 6.5 weeks or 52 Gy in 15 fractions over 3 weeks. Appropriate prescription is based on an assessment of the individual tumor.

In any event, in this embodiment, sufficient levels of radiation are employed to effect necrosis of at least part of the tumor.

In view of the above, the compositions described herein comprise from about 0.1 to about 25 weight percent of a water insoluble radioisotope having from a radioactive content of from about 0.5 microcurie to about 100 millicurie. In a preferred embodiment, the amount and radioactive content of the radioisotope is sufficient to provide for a cumulative ionizing radiation dosage at the site of implantation in a mammalian subject of from about 200 to 10,000 rads [2 to 100 Gray (Gy)].

The embolic compositions of this invention may be permanent or temporarily placed within the patient, depending upon an assessment of the tumor. If a temporary implant is warranted, a biodegradable polymer can be used which, over time, will leave only remnants of the radioactive material. Alternatively, a biodegradable or non-biodegradable polymer can be used wherein the resulting precipitate is subsequently removed from the patient, e.g., with a biocompatible solvent and catheter device. For example, during removal, a catheter is placed adjacent the polymer precipitate in the embolized vascular site. A biocompatible solvent such as DMSO is delivered to the vascular site from the catheter lumen under conditions such that the polymer precipitate dissolves in the biocompatible solvent. If desired, a second lumen in the catheter can be used to removed the resulting solution.

In such reversible placement of the radioactive embolizing compositions, the use of a water insoluble contrast agent is highly preferred because it allows the clinician to accurately visualize the position of the embolizing plug in vivo. Once visualized, the clinician can direct the tip of a microcatheter to this position and remove the plug in the manner described above.

Alternatively, a non-biodegradable polymer can be used and the polymer composition can be removed surgically along with any necrotic tissue and remaining tumor tissue.

Methods

The compositions described above can be employed in the treatment of solid mass tumors. In one such treatment, these compositions are employed in methods for the needle or catheter assisted embolization of mammalian blood vessels. The injection of the embolic composition may be performed intraoperatively or percutaneously. In such methods, a sufficient amount of this composition is introduced into the selected blood vessel via a needle or catheter delivery means under fluoroscopy so that upon precipitation of the polymer or polymerization of the prepolymer, the blood vessel is embolized. The particular amount of embolizing composition employed is dictated by the total volume of the vasculature to be embolized, the concentration of polymer/prepolymer in the composition, the rate of precipitation (solids formation) of the polymer, etc., and the total level of radiation to be delivered.

A particularly preferred method is catheter delivery of the embolizing compositions of this invention to the selected vascular site via a small diameter medical catheter. The particular catheter employed is not critical provided that polymeric catheter components are compatible with the embolizing composition (i.e., the catheter components will not readily degrade in the embolizing composition) and the catheter can be placed at the selected vascular site. In this regard, it is preferred to use polyethylene in the catheter components because of its inertness in the presence of the embolizing composition described herein. Other materials compatible with the embolizing compositions can be readily determined by the skilled artisan and include, for example, other polyolefins, fluoropolymers (e.g., Teflon™), silicone, etc.

When the polymeric composition is introduced in vivo, the biocompatible solvent diffuses rapidly into the body fluid and a solid, non-migratory precipitate forms which precipitate is the water insoluble polymer and radioisotope encapsulated therein as well as any non-radioactive water insoluble contrast agent. Without being limited to any theory, it is believed that initially, a soft gel to spongy solid precipitate forms upon contact with the body fluid. When this composition is introduced into a vascular site, the resulting precipitate restricts blood flow, entrapping red cells thereby causing clot embolization of the blood vessel.

When a prepolymeric composition is introduced in vivo, the prepolymer rapidly polymerizes in situ (less than 5 minutes) and a solid non-migratory mass forms which mass is the water insoluble polymer and radioisotope encapsulated therein as well as any non-radioactive water insoluble contrast agent. When this composition is introduced into a vascular site, the resulting mass restricts blood flow, entrapping red cells thereby causing clot embolization of the blood vessel.

In another method, the compositions of this invention can also be directly injected into a solid mass tumor by, e.g., needle delivery techniques wherein a sufficient amount of radiation is incorporated into the composition via the radioactive isotope to ablate at least a portion of the solid mass tumor.

Utility

The compositions described herein are useful in the necrosis of solid mass tumors by, for example, embolization of blood vessels leading to or in the solid mass tumor. When employed to embolized blood vessels, it is preferred that the level of radiation employed in the composition is sufficient to also ablate at least a portion of solid mass tumors. Accordingly, these compositions find use in human and other mammalian subjects requiring treatment.

Alternatively, the compositions can be delivered directly into the solid mass tumor and the radiation contained therein can be employed to effect necrosis of the tumor.

It is contemplated that these compositions can also be employed as a carrier for a chemotherapeutic agent wherein this agent is delivered in vivo for subsequent release to the solid mass tumor. Such chemotherapeutic agents are well known in the art and, include by way of example only, fluorouracil, methotrexate, cisplatin and the like. A pharmaceutical agent such as an anti-inflammatory agent, an antibiotic, and the like can be employed either in combination with the chemotherapeutic agent or as an alternative thereto.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

| | |
|---|---|
| cc = | cubic centimeter |
| cm = | centimeter |
| DMSO = | dimethylsulfoxide |
| EVOH = | ethylene vinyl alcohol copolymer |
| g = | gram |
| Gy = | gray (units for dose of radiation; 1 Gy = 1 J per kg = 100 rads) |
| ID = | internal diameter |
| in. = | inch |
| J = | joule |
| kg = | kilogram |
| mg = | milligram |
| min. = | minute |
| mL = | milliliter |
| mm = | millimeter |
| OD = | outer diameter |
| sec. = | seconds |
| μm = | micron |

Example 1

The purpose of this example is to demonstrate the preparation of polymer compositions useful in this invention. These compositions were prepared using "cold" isotopes in order to illustrate the compatibility of the compositions and suitability for delivery in vivo. It is understood that "hot" compositions could be similarly prepared.

Specifically, an EVOH polymer composition was prepared as follows:

Composition
A) 0.396 gm EVOH (48 mole percent ethylene);
B) 1.485 gm micronized tantalum; and
C) 4.95 mL DMSO.

After dissolution of the polymer at 50° C., 3 cc of this composition was then added to 0.03 g iridium powder (0.4% by weight) and the resulting composition was shaken for 4 minutes to disperse the insoluble materials. Immediately, 0.8 cc of the suspension was withdrawn via a 1 cc syringe through a 21 gauge needle. Three 0.1 cc aliquots were then injected into an excess of normal saline maintained at about 37° C. to generate the precipitate. The saline was then stirred for about 10 minutes whereupon the precipitate was examined for inner/outer consistency. In each case, a solid coherent precipitate formed in the saline.

The procedure set forth above was repeated twice. In the first instance, the amount of tantalum powder was changed to 14 weight percent and the amount of iridium powder was increased to 6 weight percent. In the second instance, the tantalum powder was removed from the composition and the amount of iridium adjusted to 20 weight percent. In each case, the total amount of tantalum/iridium was about 20 weight percent.

Both compositions, upon injection into saline, provided a solid coherent precipitate.

Example 2

The purpose of this example is to demonstrate the preparation of a prepolymer composition useful in this invention. This compositions was prepared using "cold" isotopes in order to illustrate the compatibility of the composition and suitability for delivery in vivo. It is understood that "hot" compositions could be similarly prepared.

Specifically, a cyanoacrylate-prepolymer composition was prepared by adding 500 mg of iridium non-radioactive powder (Aldrich 20968-6, 99.9% purity, screened to <25 μm) to 2 g n-butyl cyanoacrylate containing 100 ppm $SO_2$ as a stabilizer to yield a composition comprising 20% by weight of iridium. The ingredients mixed well, yielding a black/gray suspension. The iridium settled within several seconds after mixing, so constant, gentle agitation was required. In this regard, a higher viscosity cyanoacrylate composition could be used to prolong the suspension time of the iridium or, alternatively, a smaller particle size of the iridium can be used.

The mixture remained liquid with no signs of premature polymerization when evaluated at one hour after mixing and again after 12 days thereby evidencing that the iridium was compatible in this composition.

About 0.2 cc of this composition was taken up in a 1 cc syringe through a 21 gage needle and injected into about 150 cc of a 0.1 N $NaHCO_3$ aqueous solution to simulate a blood environment and cure the prepolymer. Upon injection, three small black/gray droplets were formed which immediately fell to the bottom of the container. It took about 15 minutes for the cyanoacrylate to fully cure and to be tack free.

The procedure set forth above was repeated with cyanoacrylate alone (i.e., without the iridium) and the cyanoacrylate cured in approximately the same time evidencing that the iridium was compatible with the cyanoacrylate.

Example 3

The purpose of this example is to illustrate how to conduct embolization of mammalian blood vessels leading to solid mass tumors via the methods of this invention. This example employs a rabbit with a solid mass tumor located in the upper thigh.

Specifically, a healthy male rabbit (4 kg) is implanted with cells for the VX2 tumor. After one week maturation, the tumor will have recruited blood supply from the deep femoral artery and will be about 1 cc. At this time, embolization of the tumor is conducted from a carotid artery cut down and catherization of the deep femoral artery with a 3 Fr Cook polyethylene catheter. Catheter placement is about two cm or less proximal of the tumor feed branch. The artery is then embolized by injection of sufficient amount of the 0.4% iridium composition described in Example 1 except that the iridium has a radioactive content of 150 μCi. Upon introduction at the vascular site, a solid coherent precipitate forms which comprises the polymer, the contrast agent and the iridium which precipitate embolizes the blood vessel. Over 30 days, the amount of radiation delivered internally to the rabbit is about 25 Gray and the necrotic tumor and surrounding tissue are excised for examination.

In an optional embodiment, a two lumen catheter can be reintroduced into the femoral artery and placed adjacent to the precipitate. DMSO is introduced via a first lumen whereupon the precipitate is dissolved. The second lumen is employed to remove at least a portion of the DMSO/dissolved precipitate from the vascular site by aspiration.

From the foregoing description, various modifications and changes in the composition and method will occur to those skilled in the art. All such modifications coming within the scope of the appended claims are intended to be included therein.

What is claimed is:

1. A composition suitable for treating a solid mass tumor in a mammal which composition comprises:
   (a) a biocompatible prepolymer;
   (b) an optional biocompatible solvent; and
   (c) from about 0.1 to about 25 weight percent of a water insoluble radioisotope having from a radioactive content of from about 0.5 microcurie to about 100 millicurie.

2. The composition according to claim 1, wherein said biocompatible prepolymer is selected from the group consisting of cyanoacrylates, (C1–C6)hydroxyalkyl (C1–C6) alkacrylate, and silicone prepolymers.

3. The composition according to claim 2, wherein said biocompatible prepolymer is a cyanoacrylate.

4. The composition according to claim 1, wherein said radioisotope is selected from the group consisting of $^{90}$yttrium, $^{192}$iridium, $^{198}$gold, $^{125}$iodine, $^{137}$cesium, $^{60}$cobalt, $^{55}$cobalt, $^{56}$cobalt, $^{57}$cobalt, $^{57}$magnesium, $^{55}$iron, $^{32}$phosphorus, $^{90}$strontium, $^{81}$rubidium, $^{206}$bismuth, $^{67}$gallium, $^{77}$bromine, $^{129}$cesium, $^{73}$selenium, $^{72}$selenium, $^{72}$arsenic, $^{103}$palladium, $^{203}$lead, $^{111}$indium, $^{52}$iron, $^{167}$thulium, $^{57}$nickel, $^{62}$zinc, $^{61}$copper, $^{201}$thallium, and $^{123}$iodine.

5. The composition according to claim 1 which further comprises a non-radioactive contrast agent.

6. The composition according to claim 5, wherein said non-radioactive contrast agent is water soluble.

7. The composition according to claim 6, wherein said water soluble non-radioactive contrast agent is selected from the group consisting of metrizamide, iopamidol, iothalamate sodium, iodomide sodium, and meglumine.

8. The composition according to claim 5, wherein said non-radioactive contrast agent is water insoluble.

9. The composition according to claim 8, wherein said water insoluble contrast agent is tantalum, tantalum oxide, barium sulfate, tungsten, gold and platinum.

10. A method for embolizing a blood vessel leading to or in a solid mass tumor in a mammal and causing necrosis to a portion of said solid mass tumor which method comprises:
    (a) identifying a blood vessel in said mammal which leads to or is in the solid mass tumor;
    (b) injecting a sufficient amount of an embolic composition comprising a biocompatible prepolymer, a water insoluble radioisotope and optionally a biocompatible solvent into said blood vessel under conditions wherein the prepolymer polymerizes and forms a solid mass which embolizes the blood vessel and further wherein the radioisotope is employed in an amount effective to cause necrosis of at least a portion of the tumor,
    wherein said delivery is conducted under conditions wherein said prepolymer polymerizes in situ, in the presence of the water insoluble contrast agent, at the vascular site thereby embolizing the blood vessel.

11. The method according to claim 10, wherein said biocompatible prepolymer is selected from the group consisting of cyanoacrylates, (C1–C6)hydroxyalkyl (C1–C6) alkacrylate, and silicone prepolymers.

12. The method according to claim 11, wherein said biocompatible prepolymer is a cyanoacrylate.

13. The method according to claim 10, wherein said radioisotope is selected from the group consisting of $^{90}$yttrium, $^{192}$iridium, $^{198}$gold, $^{125}$iodine, $^{137}$cesium, $^{60}$cobalt, $^{55}$cobalt, $^{56}$cobalt, $^{57}$cobalt, $^{57}$magnesium, $^{55}$iron, $^{32}$phosphorus, $^{90}$strontium, $^{81}$rubidium, $^{206}$bismuth, $^{67}$gallium, $^{77}$bromine, $^{129}$cesium, $^{73}$selenium, $^{72}$selenium, $^{72}$arsenic, $^{103}$palladium, $^{203}$lead, $^{111}$indium, $^{52}$iron, $^{167}$thulium, $^{57}$nickel, $^{62}$zinc, $^{61}$copper, $^{201}$thallium, and $^{123}$iodine.

14. The method according to claim 10, wherein said composition further comprises a non-radioactive contrast agent.

15. The method according to claim 14, wherein said non-radioactive contrast agent is water soluble.

16. The method according to claim 15, wherein said water soluble non-radioactive contrast agent is selected from the group consisting of metrizamide, iopamidol, iothalamate sodium, iodomide sodium, and meglumine.

17. The method according to claim 14, wherein said non-radioactive contrast agent is water insoluble.

18. The method according to claim 17, wherein said water insoluble contrast agent is tantalum, tantalum oxide, barium sulfate, tungsten, gold and platinum.

19. A composition suitable for treating a solid mass tumor in a mammal which composition comprises:

(a) a cyanoacrylate;

(b) an optional biocompatible solvent; and (c) from about 0.1 to about 25 weight percent of a water insoluble radioisotope having a radioactive content of from about 0.5 microcurie to about 100 microcurie.

20. A method for embolizing a blood vessel leading to or in a solid mass tumor in a mammal and causing necrosis to a portion of said solid mass tumor which method comprises:

(a) identifying a blood vessel in said mammal which leads to or is in the solid mass tumor;

(b) injecting a sufficient amount of an embolic composition comprising a cyanoacrylate, a water insoluble radioisotope and optionally a biocompatible solvent into said blood vessel under conditions wherein the cyanoacrylate polymerizes and forms a solid mass which embolizes the blood vessel and further wherein the radioisotope is employed in an amount effective to cause necrosis of at least a portion of the tumor, wherein said delivery is conducted under conditions wherein said cyanoacrylate polymerizes in situ, in the presence of the water insoluble contrast agent, at the vascular site thereby embolizing the blood vessel.

* * * * *